United States Patent
Yang et al.

(10) Patent No.: US 10,000,761 B2
(45) Date of Patent: Jun. 19, 2018

(54) **DNA MOLECULE USED FOR RECOMBINANT *PICHIA PLASMID* AND RECOMBINANT *PICHIA* STRAIN EXPRESSING PPRI PROTEIN OF *DEINOCOCCUS RADIODURANS***

(71) Applicant: SOOCHOW UNIVERSITY, Suzhou, Jiangsu (CN)

(72) Inventors: Zhanshan Yang, Suzhou (CN); Wei Wu, Suzhou (CN); Huiping Qiao, Suzhou (CN); Ling Wen, Suzhou (CN); Yi Shi, Suzhou (CN); Lili Ren, Suzhou (CN); Dong Yu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days. days.

(21) Appl. No.: 15/123,757

(22) PCT Filed: May 30, 2014

(86) PCT No.: PCT/CN2014/078900
§ 371 (c)(1),
(2) Date: Sep. 6, 2016

(87) PCT Pub. No.: WO2015/158031
PCT Pub. Date: Oct. 22, 2015

(65) Prior Publication Data
US 2017/0016009 A1    Jan. 19, 2017

(30) Foreign Application Priority Data
Apr. 16, 2014 (CN) .......................... 2014 1 0153614

(51) Int. Cl.
| | | |
|---|---|---|
| *C12N 15/81* | (2006.01) | |
| *C07K 14/195* | (2006.01) | |
| *C12N 9/52* | (2006.01) | |
| *A61K 38/00* | (2006.01) | |

(52) U.S. Cl.
CPC .......... *C12N 15/815* (2013.01); *C07K 14/195* (2013.01); *C12N 9/52* (2013.01); *A61K 38/00* (2013.01)

(58) Field of Classification Search
None
See application file for complete search history.

(56) References Cited

U.S. PATENT DOCUMENTS

2011/0236933 A1* 9/2011 Yang .................... C07K 14/195
                                                                       435/91.41
2013/0011909 A1* 1/2013 Urbatsch ................ C12N 15/11
                                                                       435/254.21

FOREIGN PATENT DOCUMENTS

| CN | 101492651 A | 7/2009 |
|---|---|---|
| CN | 101671679 A | 3/2010 |
| CN | 103555749 A | 2/2014 |

OTHER PUBLICATIONS

Cereghino et al. (Curr. Opin. Biotechnol. 13, 4, 329-332, 2002).*
Close et al. (Genetic Eng.—Basics, New Appl. and Responsibilities, Barrera-Saldana (Ed.), ISBN:978-953-307-790-1, InTech, 2012, Available from: http://www.intechopen.com/books/genetic-engineering-basics-new-applications-and-responsibilities/expression of non-native genes in a surrogate-host-organism.*
Hochuli et al. (Nature Biotech., 6 (11): 1321-25, 1988).*
Huiming Lu et al.; DNA binding is essential for PprI funcation in response to radiation damage in *Deinococcus radiodurans*; DNA Repair 11 (2012) 139-145.
Yongqin Zhang et al.; Expression and purification of PprI protein from *D. radiodurans* R1 in *Escherichia coli*; J. Radiat. Res. Radiat. Process. vol. 29, No. 2, Apr. 2011, 117-122.
Guanjun Gao et al.; Expression of *Deinococcus radiodurans* PprI enhances the radioresistance of *Escherichia coli*; DNA Repair 2 (2003) 1419-1427.
Wei Wu; Abstract of Master Thesis: Study of the expression, fermentation, and purification PprI protein form *Deinococcus radiodurans* in the *Pichia pastories*; Soochow University, Apr. 2013.
Yi Shi, et al. The protein PprI provides protection against radiation injury in human and mouse cells. Scientific Reports, 2016 6:26664,DOI:10.1038/srep26664.
Ting-ting et al, The effects of pprI gene of *Deinococcus radiodurans* R1 on acute radiation injury of mice exposed to 60Co γ -ray radiation. Oncotarget. Jan. 10, 2017; 8(2): 2008-2019.
Ling Wen, et al., *Deinococcus radiodurans* pprI expression enhances the radioresistance of eukaryotes. Oncotarget. Mar. 29, 2016; 7(13): 15339-15355.

* cited by examiner

*Primary Examiner* — Nancy A Treptow
(74) *Attorney, Agent, or Firm* — SZDC Law P.C.

(57) ABSTRACT

A DNA molecule comprising the sequence set forth in SEQ ID NO: 1, a recombinant *Pichia* plasmid into which the DNA molecule is inserted, and a recombinant *Pichia* strain obtained by the transformation of the recombinant *Pichia* plasmid into a competent *Pichia* cell and efficiently expressing the PprI protein of *Deinococcus radiodurans*.

9 Claims, 7 Drawing Sheets

DNA MOLECULE USED FOR RECOMBINANT *PICHIA* PLASMID AND RECOMBINANT *PICHIA* STRAIN EXPRESSING PPRI PROTEIN OF *DEINOCOCCUS RADIODURANS*

The present application is a national phase of International Application No. PCT/CN2014/078900, filed on May 30, 2014, which claims the priority of Chinese Patent Application No. 201410153614.3, titled "A DNA MOLECULE, RECOMBINANT PICHIA PLASMID AND RECOMBINANT PICHIA STRAIN EFFICIENTLY EXPRESSING PPRI PROTEIN OF DEINOCOCCUS RADIODURANS" filed with the Patent Office of China on Apr. 16, 2014, the contents of which are incorporated herein by reference in its entirety.

FIELD OF THE INVENTION

The present invention relates to the field of biotechnology, specifically to a DNA molecule, a recombinant *Pichia* plasmid and a recombinant *Pichia* strain efficiently expressing PprI protein of *Deinococcus radiodurans*.

BACKGROUND OF THE INVENTION

In nuclear emergencies such as nuclear accidents, nuclear terrors and nuclear wars, ionizing radiation can cause serious acute radiation injury (ARI) in humans. Treatment and prevention of the radiation-induced injuries concerns peaceful uses of atomic energy and national nuclear safety, and thus studies in this field has become a research field which receives high attention and significant investment from governments and scholars around the world.

*Deinococcus radiodurans* (DR) is a prokaryotic bacterium having the strongest radioresistance found on the earth to date, and the extremely strong radioresistance of this bacterium is associated with its own perfect and efficient DNA repair system, in which a plurality of DNA repair genes and proteins thereof play a crucial role in its specific radioresistance. In 1999, White et al. have firstly disclosed the gene sequence of DR, wherein an inducer of pleiotropic proteins promoting DNA repair (pprI) is one radioresistant gene having important regulatory effect in the *Deinococcus radiodurans*. PprI gene contains 987 bp, and encodes 328 amino acids (AAs), and from which the product PprI protein is encoded by DR_0167, with a molecular weight of 37 KD. Recent studies have shown that, pprI gene is the master switch gene for controlling the DNA repair and protection pathways of *Deinococcus radiodurans*; and after radiation of *Deinococcus radiodurans*, the PprI protein could up-regulate the expression of over 210 genes via multiple signaling pathways, in which 21 genes associated with DNA repair and replication are included [H Lu, H Chen, G Xu, et al. DNA Repair, 2012, 11(2):139-145]. In the past more than 50 years from the discovery of *Deinococcus radiodurans*, intensive studies on the function of the genes and proteins of *Deinococcus radiodurans* as well as the mechanisms thereof have been carried out by scholars around the world. However, to date, these studies only focus on prokaryotic cells, that is, *Deinococcus radiodurans* itself or *Escherichia Coli*.

In Chinese patent application No. 200910003512.2, a eukaryotic expression recombinant plasmid pCMV-HA-pprI from *Deinococcus radiodurans* pprI gene was firstly constructed, which was transformed into a human embryo kidney HEK-293T cell and a radiated mammal to successfully express PprI protein, which has very significant preventive and therapeutic effect on fatal acute radiation injury in animals, suggesting that the PprI protein has potential to become a new biological agent for prevention and treatment of acute radiation injury. However, presently, from the eukaryotic expression recombinant plasmid pCMV-HA-pprI in this patent, it is still difficult to obtain efficiently and massively expressed and purified PprI protein via human cell engineering.

A prokaryotic expression system *Escherichia Coli* can be used for efficient expression and purification of PprI protein [ZHANG Yongqin, ZHOU Hui, CHEN Jie, YANG Zhanshan, JOURNAL OF RADIATION RESEARCH AND RADIATION PROCESSING, 2011, 29(2): 117-122]; however, such a method have many defects in that: 1. the expressed protein is not subjected to post-translational modification such as glycosylation, resulting in a decreased activity; 2. the expressed protein is present in the form of inclusion body, which also results in a decreased activity of the protein upon extraction through denaturation; 3. there may be endotoxins and toxic proteins from *Escherichia Coli* itself blended in the protein product of interest, resulting in unexpected toxicity.

Yeast is one of eukaryotic expression systems commonly used in gene engineering, among which *Pichia pastoris* is one of yeast engineering strains using methanol as the sole carbon source. Such yeast has the following advantages: 1. such yeast is simple in genetic manipulation, has a highly stable genome, and can express an exogenous gene at a high level; 2. such yeast can proceed post-translational modifications of a protein, such as glycosylation, disulfide bond formation, signal peptide cleavage, etc.; 3. the expression vector does not contain a yeast replication origin, the exogenous gene is homologously recombined into the chromosome of a yeast cell and exists stably, and the integrated exogenous gene can passage stably along with the growth of yeast.

If the *Deinococcus radiodurans* PprI protein can be expressed and purified by the eukaryotic expression system *Pichia*, the defects of expression and purification of PprI protein with a human cell or a prokaryotic expression system *Escherichia Coli* in the prior art will be improved or solved. However, *Deinococcus radiodurans* belongs to prokaryotic organism, which has huge differences in phylogenetic evolution from the eukaryotic organism *Pichia*, for example, significant differences in gene and protein composition and function, amino acid codon preference of a protein and other aspects. Therefore, if a *Deinococcus radiodurans* PprI gene is directly constructed into a *Pichia* expression system via gene engineering, as demonstrated by pre-experimental studies, it is impossible and also is adverse to efficiently express the *Deinococcus radiodurans* PprI protein, which problem cannot be successfully solved easily in accordance with the general genetic modification techniques in the art.

Therefore, the present invention provides a technology for successful expression and purification of PprI protein of *Deinococcus radiodurans* R1 via an eukaryotic expression system *Pichia*, which will establish a solid basis for further studies on functions, mechanisms and applications of this protein, make up for the blank that there has yet been no radioresistant prokaryotic protein drug in the field of treatment and prevention of radiation injury internationally, and rises to the internationally advanced ranks in studies on original protein drugs as radioprotective agents.

SUMMARY OF THE INVENTION

In view of this, an object of the present invention is to provide a new synthesized DNA molecule which enables the DNA molecule to successfully and efficiently express and purify PprI protein via *Pichia pastoris*.

In addition, the present invention further provides a recombinant plasmid comprising the DNA molecule and a recombinant *Pichia* strain efficiently expressing the PprI protein of *Deinococcus radiodurans*, which can also achieve the object of the present invention.

In order to achieve the above objects of the invention, the present invention provides the following technical solutions.

A DNA molecule, which comprises the nucleotide sequence set forth in SEQ ID NO: 1.

In the present invention, the sequence of the Open Reading Frame (ORF) in the pprI gene (DR_0167, Gene ID: 1798483) of *Deinococcus radiodurans* R1 is optimized and modified to encode and synthesize a new pprI gene, i.e. the nucleotide sequence set forth in SEQ ID NO: 1, which is called "Pi-pprI gene" to be distinguished from the original pprI gene, provided that the amino acid sequence of PprI protein keeps constant.

A DNA molecule comprising the nucleotide sequence set forth in SEQ ID NO: 1, as described herein, means that, in addition to the nucleotide sequence set forth in SEQ ID NO: 1, some sequences such as a 6× His tag sequence for convenient separation and purification of protein can be added. Those skilled in the art are able to connect these sequences which do not affect the normal expression of the Pi-pprI gene with the Pi-pprI gene sequence according to the prior art, which can be achieved for those skilled in the art.

In addition, for those skilled in the art, according to the cleavage site into which a plasmid is to be actually inserted, corresponding cleavage sites can be added at both ends of the DNA molecule, and other suitable tag sequences which are not limited to the 6× His tag sequence as mentioned herein can also be selected. After the present invention provides the sequence of the key Pi-pprI gene, these selections all can be achieved according to the prior art, which similarly does not go beyond the scope of the core technology in the present invention.

Preferably, the nucleotide sequence set forth in SEQ ID NO: 1 is obtained by Overlapping PCR amplification from the primers of nucleotide sequences set forth in SEQ ID NOs: 2-41. In the present invention, the overlapped portions of a series of overlapped 42s (hereinafter abbreviated as p-1 to p-40) of the nucleotide sequences set forth in SEQ ID NOs: 2-41 are complementarily annealed to form a template DNA, then the nucleotide sequence set forth in SEQ ID NO: 1 is synthesized and obtained by Overlapping PCR method. FIG. 1 shows a schematic diagram of Overlapping PCR amplification.

Preferably, by the above preparation method, three fragments are synthesized and obtained with the primers (p-1 to p-16) of the nucleotide sequences set forth in SEQ ID NOs: 2-17, the primers (p-15 to p-28) of the nucleotide sequences set forth in SEQ ID NOs: 16-29 and the primers (p-27 to p-40) of the nucleotide sequences set forth in SEQ ID NOs: 28-41, respectively, and then a full DNA molecule is formed by amplifying with the primer (p-1) of the nucleotide sequence set forth in SEQ ID NO: 2 and the primer (p-40) of the nucleotide sequence set forth in SEQ ID NO: 41.

Preferably, the Overlapping PCR method is performed under the following synthesis conditions: 98° C. for 30 s, 58° C. for 30 s, 72° C. for 1 min, for totally 25 cycles; and finally 72° C. for 7 min. The reaction system is as follows:

| | |
|---|---|
| p-1 (10 µmol/l) | 1 µl |
| p-n (10 µmol/l) | 1 µl |
| p-2 to p-(n − 1)(1 µmol/l) | each 1.5 µl |
| 5 × PrimeSTAR ® Buffer | 10 µl |
| dNTPs (2.5 mmol/l) | 4 µl |
| PrimeSTAR ® HS DNA Polymerase | 0.5 µl |
| ddH$_2$O | added to a total volume of 50 µl |

Preferably, the DNA molecule of the present invention comprises the nucleotide sequence set forth in SEQ ID NO: 1 and a 6× His tag sequence, in which the 6× His tag sequence is located at the 5'-end of the nucleotide sequence set forth in SEQ ID NO: 1, which DNA molecule is prepared according to the following method.

Using a DNA molecule comprising the nucleotide sequence set forth in SEQ ID NO: 1 as the template, PCR amplification is performed using a primer of a nucleotide sequence set forth in SEQ ID NO: 42 bearing a 6× His tag sequence and a primer of a nucleotide sequence set forth in SEQ ID NO: 41, to obtain a DNA molecule comprising the nucleotide sequence set forth in SEQ ID NO: 1 and the 6× His tag sequence.

The PCR amplification is carried out under the following conditions: 95° C. for 5 min; 94° C. for 30 s, 50° C. for 30 s, 72° C. for 90 s, for totally 30 cycles; and finally 72° C. for 10 min, then kept at 4° C.

Meanwhile, the present invention further provides a recombinant *Pichia* plasmid obtained by insertion of a DNA molecule comprising a nucleotide sequence set forth in SEQ ID NO: 1 into a *Pichia* expression plasmid.

Preferably, the recombinant *Pichia* plasmid is obtained by insertion of a DNA molecule comprising a nucleotide sequence set forth in SEQ ID NO: 1 and a 6× His tag sequence between the Cpo I and the Not I cleavage sites in pHBM-905A plasmid, in which the 6× His tag sequence is located at the 5'-end of the nucleotide sequence set forth in SEQ ID NO: 1. A schematic diagram of construction of the recombinant *Pichia* plasmid of the present invention is shown in FIG. 2.

In addition, the present invention further provides a recombinant engineered *Pichia* strain obtained by transformation of any one of the recombinant *Pichia* plasmids of the present invention into a competent *Pichia* cell.

Preferably, the recombinant engineered *Pichia* strain is obtained by linearization of the recombinant *Pichia* plasmid by Sal I cleavage, and then electrotransformation into a competent *Pichia* GS115 cell.

Through detection via gel electrophoresis and sequencing, a fragment having identical size and sequence to the nucleotide sequence set forth in SEQ ID NO: 1 can be successfully amplified with the recombinant *Pichia* plasmid of the present invention, the amino acid sequence encoded therefrom is identical to the PprI protein of *Deinococcus radiodurans* with a relative molecular mass of 43 KD, as demonstrated by SDS-PAGE electrophoresis, Western blotting and mass spectrometry. Meanwhile, a band for PprI protein secretory expression can be detected 24 hours after inducing the expression from the recombinant engineered *Pichia* strain with methanol. Preferably, for induction of the protein expression at a methanol final concentration of is 1%, at a temperature of 30° C., pH 6.0, the protein of interest has the highest expression of 0.35 mg/ml at 120 h after induction. The result of the above detections shows that, the PprI protein can be successfully expressed and secreted in *Pichia* with the DNA molecule, recombinant *Pichia* plasmid and recombinant engineered *Pichia* strain provided in the present invention, which demonstrates that the DNA molecule is useful for the preparation of recombinant *Pichia* plasmids, recombinant engineered *Pichia* strains and medicament against radiation damages.

From the above-mentioned technical solutions, the sequence of the pprI gene of *Deinococcus radiodurans* is optimized and engineered, provided that the amino acid sequence of PprI protein keeps constant, to encode a new pprI gene, which allows successful construction of a recombinant *Pichia* plasmid and a recombinant engineered *Pichia* strain, as well as expression and secretion of the PprI protein, establishing a solid basis for further application of the yeast fermentation system to massively and efficiently prepare protein medication against radiation damage.

DETAILED EMBODIMENTS

Figure 1:
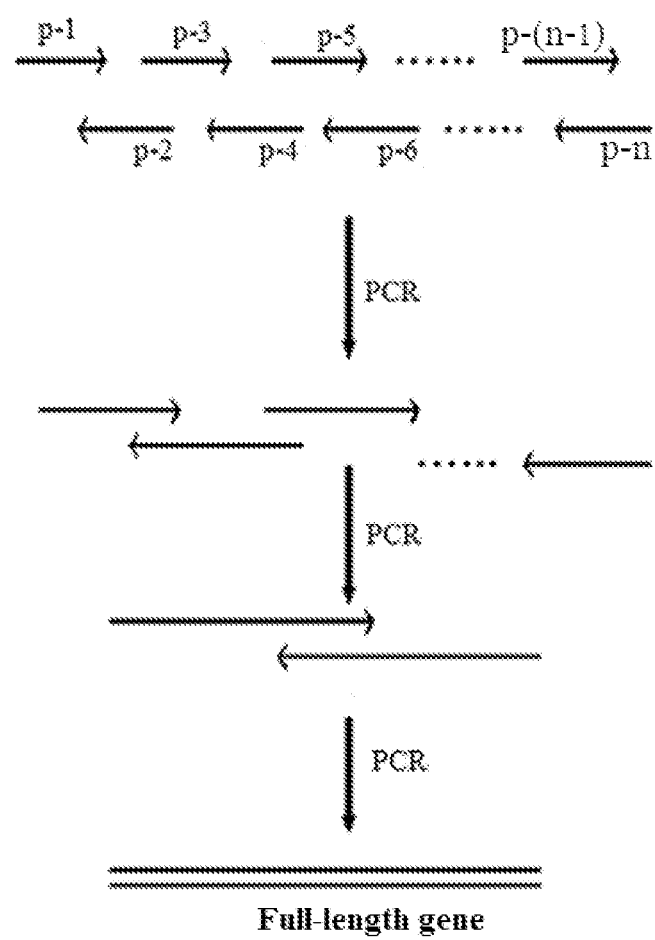
FIG. 1 shows a schematic diagram of Overlapping PCR amplification.

The present invention discloses a DNA molecule as well as a recombinant *Pichia* plasmid and a recombinant *Pichia* strain efficiently expressing the PrpI protein of *Deinococcus radiodurans*. In view of the disclosure herein, these can be achieved by suitably improving process parameters for those skilled in the art. It is in particular to be noted that, all the similar substitutions or modifications are obvious for those skilled in the art, which will all be deemed to be included in the present invention. The DNA molecule, recombinant *Pichia* plasmid and recombinant *Pichia* strain of the present invention have been described with preferred examples, and related artisans can make modifications or suitable alterations and combinations to achieve and apply the technology of the present invention without departing from the content, spirit and scope of the present invention.

Test materials used in the examples are as follows:

1. Strains and Plasmids

*Escherichia coli* strain XL10-GOLD and *Pichia pastoris* strain GS115 were purchased from Invitrogen; *Pichia* expression vector pHBM-905A (8923 bp) was gifted by Professor M A Lixin from Hubei University (M A Lixin, ZHAO Xixuan, CHEN Wanping, L I Yexing, F U Ling, Y A O Yonglan. A METHOD FOR IN VITRO EFFICIENT CONSTRUCTION OF MULTI-COPY *PICHIA* EXPRESSION VECTOR. Patent Application No.: 201210591987.X), with a plasmid profile set forth in FIG. 2.

2. Reagents and Culture Media

Taq DNA polymerase, restriction endonuclease, T4 DNA ligase, etc. were all purchased from TaKaRa Biotechnology (Dalian) Co., Ltd. Plasmid DNA extraction kit and DNA fragment gel recovery kit were both purchased from Axygen Biotechnology (Hangzhou) Co., Ltd. DNA molecular weight standards were purchased from Beijing SBS Genetech Co., Ltd. Protein molecular weight standards were purchased from Bio-Rad Laboratories, Inc. Yeast nitrogen base (YNB) was purchased from DIFCO Corp. Mouse-derived anti-His tag antibody was a product from SIGMA Corporation. HRP-crosslinked rabbit anti-murine antibody was a product from Invitrogen Corporation. ECL chemiluminescence kit was purchased from Millipore Corporation. Other reagents were all chemically pure or analytically pure products made in China.

*Escherichia coli* culture medium: LB: 1% peptone, 0.5% yeast extract, 1% NaCl, pH 7.0.

Yeast culture medium: YPD plate (with each 100 ml double-distilled water solution containing 1 g of yeast extract, 2 g of peptone, 2 g of glucose and 2 g of agar powder), BMGY (with each 100 ml double-distilled water solution containing 1 g of yeast extract, 2 g of peptone, 1.34 g of TNB and 1 ml of glycerol), BMMY (with each 100 ml double-distilled water solution containing 1 g of yeast extract, 2 g of peptone, 2 g of glucose and 1 ml of methanol), were purchased from Shanghai root biological technology limited company.

The present invention will be further illustrated as follows, in conjunction with examples.

EXAMPLE 1

Optimization and Synthesis of the DNA Molecule of the Present Invention

In the present invention, the sequence of an Open Reading Frame (ORF) in the pprI gene (DR_0167, Gene ID: 1798483) of *Deinococcus radiodurans* R1 was optimized and modified to encode and synthesize a new pprI gene (Pi-pprI gene), i.e. the nucleotide sequence set forth in SEQ ID NO: 1, so as to efficiently express the protein of interest, provided that the amino acid sequence of PprI protein kept constant.

1. Synthetic Method

In the present invention, a series of overlapped primers of nucleotide sequences set forth in SEQ ID NOs: 2-41 were designed and synthesized in accordance with an artificially designed Pi-pprI gene, and then a DNA molecule comprising the nucleotide sequence set forth in SEQ ID NO: 1 and carrying a Cpo I restriction endonuclease site and a Not I restriction endonuclease site (so as to be convenient for subsequent construction of a recombinant plasmid) was synthesized and obtained by Overlapping PCR. The specific method is as follows:

By Overlapping PCR with the primers (p-1 to p-16, 404 bp) of the nucleotide sequences of SEQ ID NOs: 2-17, the primers (p-15 to p-28, 370 bp) of the nucleotide sequences of SEQ ID NOs: 16-29 and the primers (p-27 to p-40, 330 bp) of the nucleotide sequences of SEQ ID NOs: 28-41, respectively, three fragments were synthesized and obtained, which were fragment 1, fragment 2 and fragment 3 sequentially.

After synthesis of the three fragments, with these three fragments as templates, amplification was performed with the primer (p-1) of the nucleotide sequence of SEQ ID NO: 2 and the primer (p-40) of the nucleotide sequence of SEQ ID NO: 41, to form the entire DNA molecule.

Figure 3:
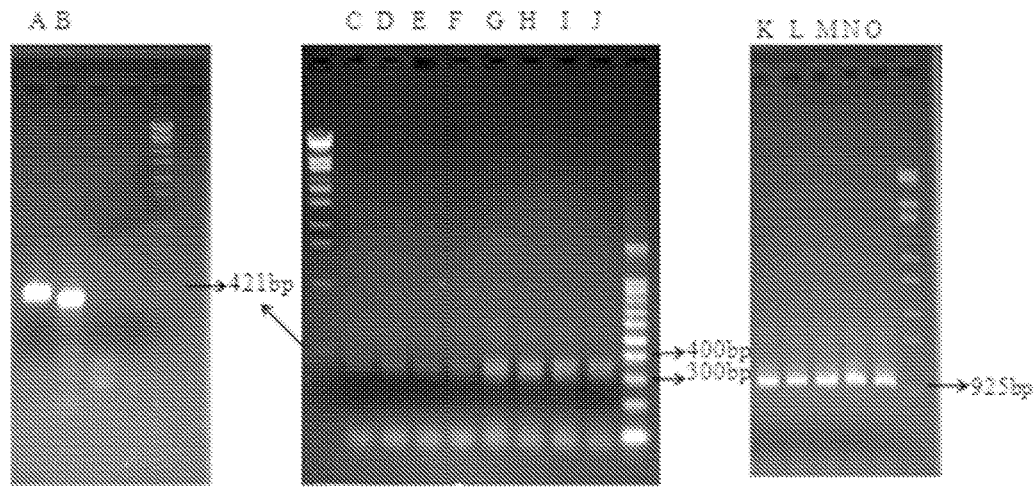
FIG. 3 shows graphs of agarose gel electrophoresis of the DNA molecule, wherein lanes A-B are fragments 1 and 2; lanes C-J are fragment 3; lanes K-O are full-length Pi-pprI gene, with arrows indicating the size (bp) of bands for DNA molecular weight standards.

From detection by agarose gel electrophoresis, the DNA molecule had a size in line with expectations, and the agarose gel electrophoretogram is shown in FIG. 3.

Wherein, the Overlapping PCR method was performed under the following synthesis conditions: 98° C. for 30 s, 58° C. for 30 s, 72° C. for 1 min, for totally 25 cycles; and finally 72° C. for 7 min. The reaction system (50 μl) was as follows:

| | |
|---|---|
| p-1 (10 μmol/l) | 1 μl |
| p-n (10 μmol/l) | 1 μl |
| p-2 to p-(n − 1)(1 μmol/l) | each 1.5 μl |
| 5 × PrimeSTAR ® Buffer | 10 μl |
| dNTPs (2.5 mmol/l) | 4 μl |
| PrimeSTAR ® HS DNA Polymerase | 0.5 μl |
| ddH$_2$O | added to a total volume of 50 μl |

The PCR amplification was carried out under the following conditions: initial denaturation at 95° C. for 5 min; denaturation at 94° C. for 30 s, annealing at 50° C. for 30 s, extension at 72° C. for 90 s, for totally 30 cycles; and finally extension at 72° C. for 10 min, then kept at 4° C.

EXAMPLE 2

Synthesis of a DNA Molecule (Introduced with a 6× his Tag Sequence) of the Present Invention With the DNA molecule obtained in Example 1 as the template, a PCR amplification was carried out with the primer of a nucleotide sequence of SEQ ID NO: 42 carrying a 6 × His tag sequence and a primer of a nucleotide sequence of SEQ ID NO: 41, to obtain a DNA molecule comprising a nucleotide sequence set forth in SEQ ID NO: 1 and a 6 × His tag sequence (carrying a Cpo I restriction endonuclease site and a Not I restriction endonuclease site). Wherein, the primer SEQ ID NO:42 was obtained by introduction of a 6 × His tag sequence based on the primer p-1.

The PCR amplification was carried out under the following conditions: initial denaturation at 95° C. for 5 min; denaturation at 94° C. for 30 s, annealing at 50° C. for 30 s, extension at 72° C. for 90 s, for totally 30 cycles; and finally extension at 72° C. for 10 min, then kept at 4° C.

Figure 4:
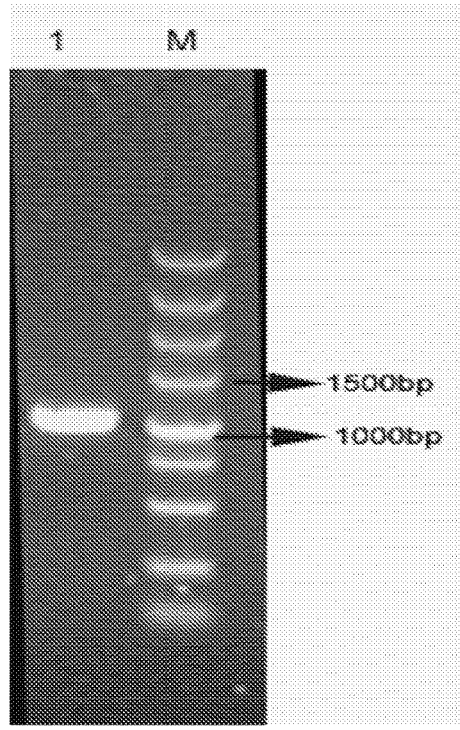
FIG. 4 shows a graph of agarose gel electrophoresis of the DNA molecule introduced with a 6× His tag sequence, wherein 1 is PCR amplification product, and M is Marker.

3 μl of the PCR amplification product was detected by 0.8% agarose gel electrophoresis, and the results showed that the PCR amplification product has a size (1005 bp) in line with expectations, and the agarose gel electrophoretogram thereof is shown in FIG. 4.

EXAMPLE 3

Construction of a Recombinant *Pichia* Plasmid

A *Pichia* expression vector pHBM905A (8923 bp) was subjected to double digestions by Cop I and Not I enzymes, separated by agarose gel electrophoresis, and the large fragment (7719 bp) was recovered by cutting the gel.

Figure 2:
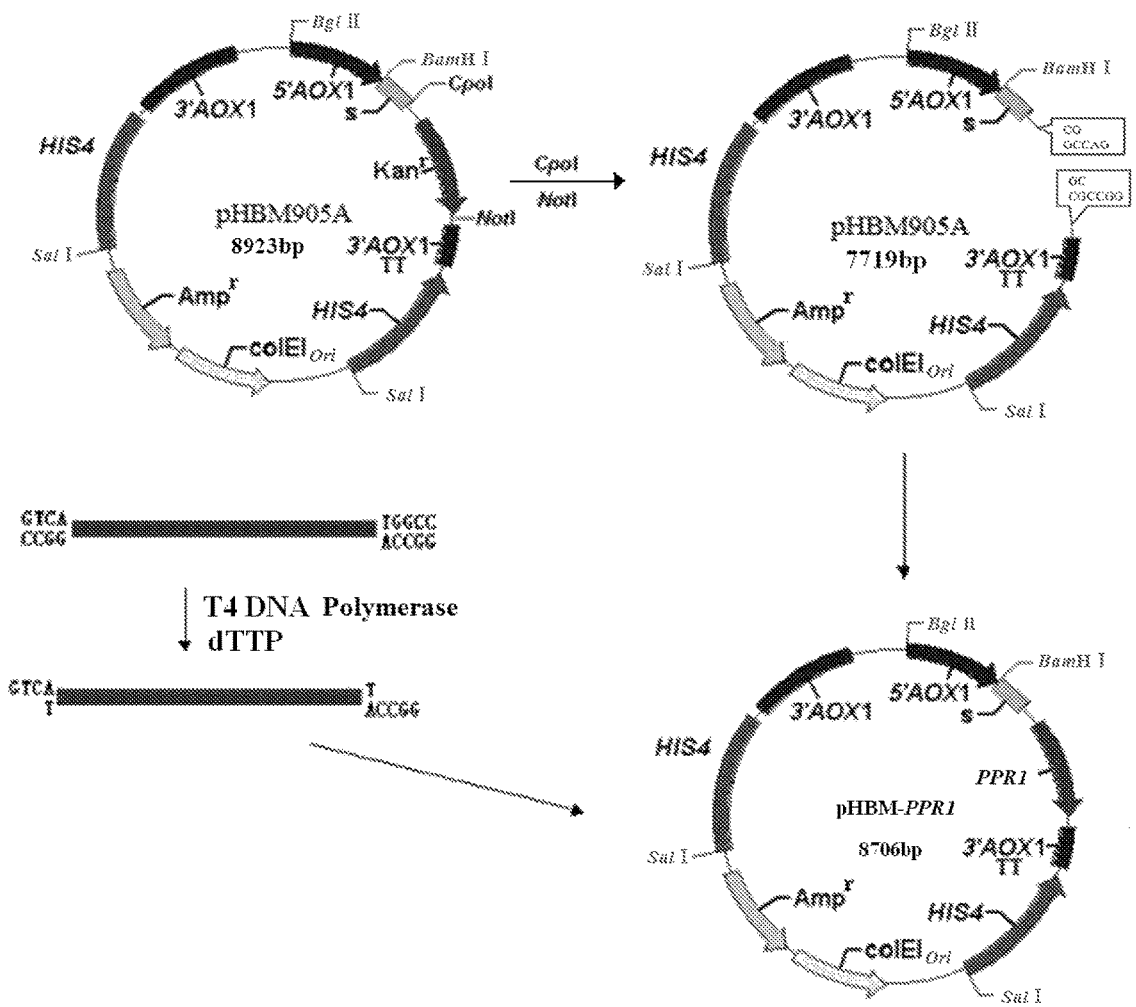
FIG. 2 shows a schematic diagram of construction of a recombinant *Pichia* plasmid.

The PCR product (1005 bp) synthesized in Example 2 was treated with T4 DNA polymerase in the presence of dTTP, and then ligated with the large fragment recovered by cutting the gel, to obtain a *Pichia* recombinant expression plasmid pHBM-905A-Pi-pprI (8706 bp), abbreviated as pHBM-Pi-pprI, and the construction process is shown in FIG. 2.

EXAMPLE 4

Identification of the *Escherichia coli* Transformant

In order to confirm whether the constructed recombinant *Pichia* plasmid was constructed successfully, it was transformed into *Escherichia coli*, and then identified.

1. Bacteria-Boiled PCR Identification

Figure 5:
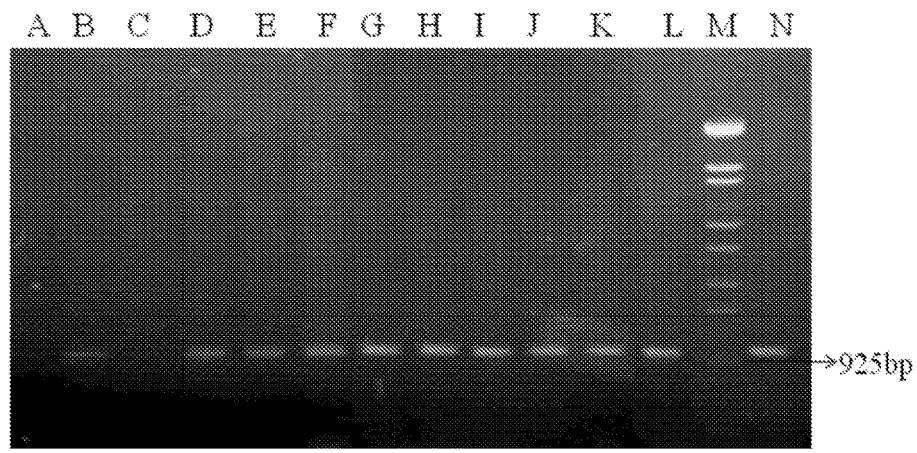
FIG. 5 shows a graph of agarose gel electrophoresis for PCR verification of the *Escherichia coli* recon Pi-pprI gene, wherein lane A is a negative control, i.e. no transformed *Escherichia coli* template was added; lanes B-L are the PCR products with transformed *Escherichia coli* as the template; lane N is the PCR product with Pi-pprI gene as the template (positive control).

11 Transformant Colonies were Randomly Selected on the *Escherichia Coli* transformation plate, and separately transferred into 1.5 ml Eppendorf tubes containing 20 μl of sterile water, placed in a boiling water bath for 3 min and then cooled in an ice bath. After high speed centrifugation (14,000 rpm) for 1 min, 1-2 μl of the supernatant was taken to perform PCR amplification with primers p-1 and p-40. The PCR products were detected by agarose gel electrophoresis, set forth in FIG. 5. Results showed that, 10 of 11 transformants can give the genes synthesized in Example 2.

2. Agarose Gel Electrophoresis of the Plasmid DNA from the Transformant

Figure 6:
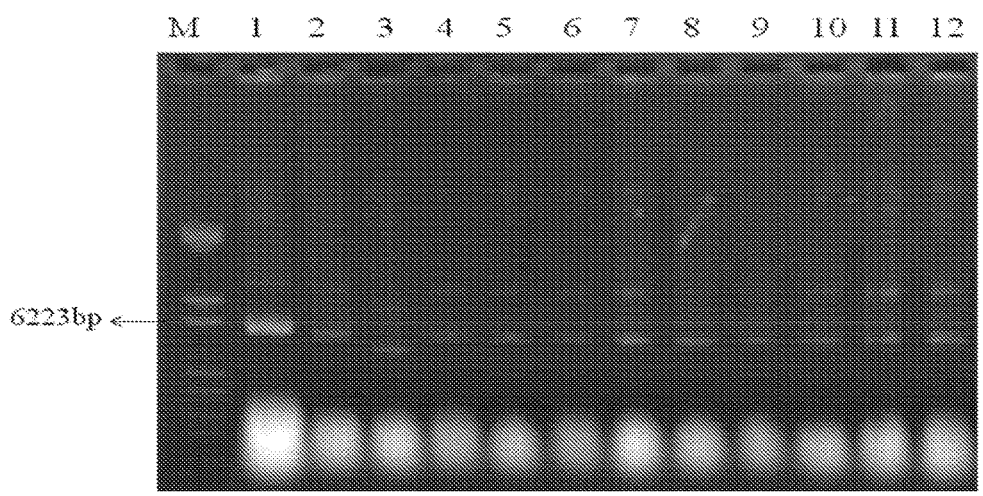
FIG. 6 shows a graph of agarose gel electrophoresis for the plasmid DNA of the *Escherichia coli* recon, wherein lane 1 is pHBM905A plasmid (negative control), which plasmid has a stuffer fragment of 1200 bp in its multiple cloning site; lanes 2-12 are plasmids for single colonies corresponding to B-L in FIG. 5.

The selected 11 transformant colonies were extracted for plasmid DNA with an AXYGEN plasmid MiniPrep kit, and subjected to detection with agarose gel electrophoresis, set forth in FIG. 6. Results showed that, 10 of 11 transformants are recombinant plasmids with the same size.

3. Sequencing Identification of the Plasmid DNA from the Transformant

Three recombinant plasmids, which were correct by colony PCR identification and plasmid size comparison, were randomly selected and were subjected to sequencing. Results showed that, the inserted pprI gene encoding sequence has a nucleotide sequence completely identical to that of the artificial synthesized SEQ ID NO: 1. The designed and synthesized Pi-pprI (the nucleotide sequence set forth in SEQ ID NO: 1) gene encoding sequence is completely different from the pprI gene encoding sequence (DR_0167, the nucleotide sequence set forth in SEQ ID NO: 43) from the original *Deinococcus radiodurans* R1.

4. Analysis Results of Bioinformatics Software

The Pi-pprI (the nucleotide sequence set forth in SEQ ID NO: 1) gene sequence was analyzed by using bioinformatics software (www.bio-soft.net/sms/index.html), and results showed that the amino acid sequence encoded therefrom is completely identical to that (an amino acid sequence set forth in SEQ ID NO: 44) of PprI protein (NP_293891.1) encoded from pprI gene of *Deinococcus radiodurans* R1.

Based on the above detection results, from *Escherichia coli* transformed with the recombinant *Pichia* plasmid, plasmids can be extracted, which have a correct band position and size, the sequencing result thereof is the same as that of the Pi-pprI (the nucleotide sequence set forth in SEQ ID NO: 1) gene sequence, and the Pi-pprI gene sequence can correctly express PprI protein, illustrating that the plasmid has been constructed successfully.

EXAMPLE 5

Establishment of a Recombinant Engineered *Pichia* Strain

Figure 7:
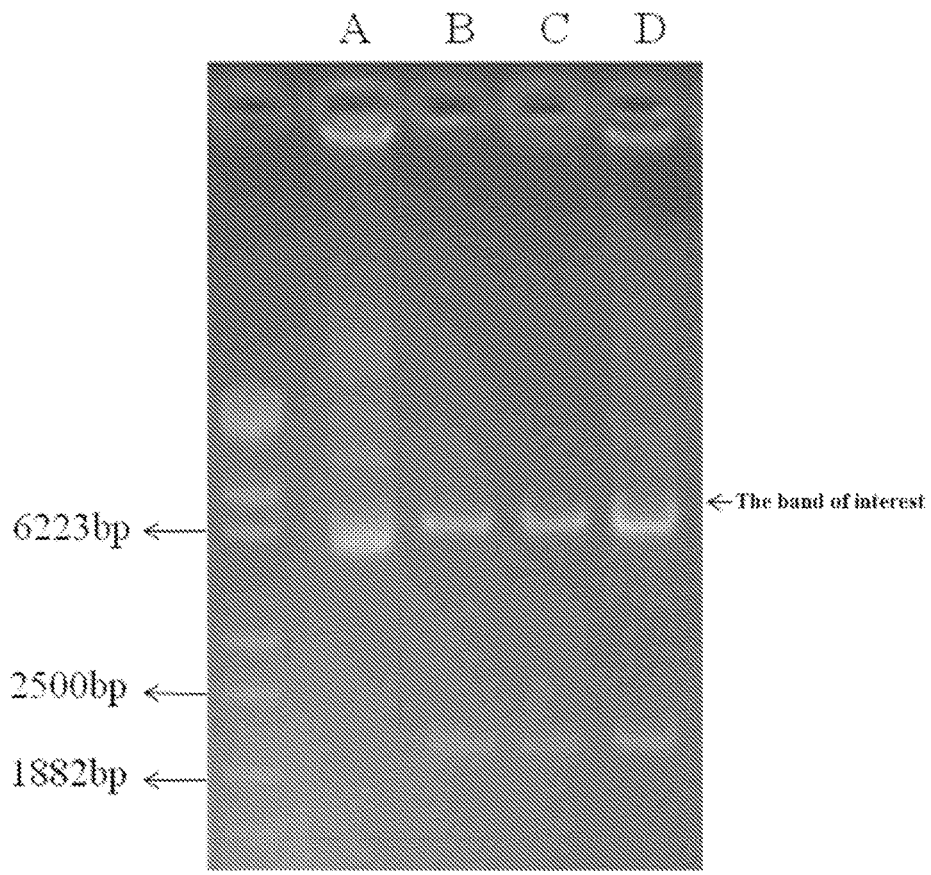
FIG. 7 shows pHBM-Pi-pprI and the Sal I restriction map thereof, wherein lane A is the recombinant plasmid pHBM-Pi-pprI and lanes B-D are Sal I restriction map of the recombinant plasmid pHBM-Pi-pprI.

The recombinant *Pichia* plasmid pHBM-Pi-pprI which was sequenced to be correct, was linearized with Sal I enzyme (with an agarose gel electrophoretogram set forth in FIG. 7), followed by electro-transformation into competent *Pichia* GS115 cells, to obtain a recombinant engineered *Pichia* strain (pHBM-Pi-pprI *Pichia* transformant). The preparation of the competent *Pichia* cells was performed in accordance with the operation manual of Invitrogen (see, www.pdffactory.com).

The electrotransformation experiment was carried out with the following related parameters: Voltage Booster: 4 kΩ, Capacitance: 50 µF, DC VOLTS: 410, Charge Rate: Fast.

Figure 8:
FIG. 8 shows a graph of agarose gel electrophoresis for PCR verification of a pHBM-Pi-pprI *Pichia* transformant, wherein lane A is the PCR product with the pHBM905A plasmid as the template (negative control); lane 2 is the PCR product with the recombinant plasmid pHBM-Pi-pprI as the template (positive control); and lanes 3-16 are the PCR products with the pHBM-Pi-pprI *Pichia* transformant as the template.

The electrotransformed *Pichia* cells were coated onto a MD plate (MD: 1.34% YNB; 4×10-5% biotin, 2% glucose), then cultured at 28° C. for 2-3 days. The yeast transformant colonies on the MD plate were randomly selected and subjected to bacteria-boiled PCR identification. Primers used in the bacteria-boiled PCR were p-1 and p-40. PCR results showed that, in all the 14 *Pichia* transformants, the Pi-pprI (the nucleotide sequence set forth in SEQ ID NO: 1) gene sequence of 987 bp can be amplified (with the electrophoretogram set forth in FIG. 8), illustrating a successful transformation.

EXAMPLE 6

Induction Expression of PprI Protein from a Recombinant Engineered *Pichia* Strain (pHBM-Pi-pprI *Pichia* Transformant)

pHBM-Pi-pprI *Pichia* transformants which were identified to be positive, were selected and subjected to induction expression by shake-flask culture. A negative control strain was a transformant which was obtained by linearizing a empty vector plasmid pHBM-905A with Sal I enzyme followed by transformation into a *Pichia* GS115 strain. The method was as follows:

(1) A single colony of a pHBM-Pi-pprI *Pichia* transformant was selected, inoculated into 50 ml of BMGY liquid medium (charged at 10%, i.e., 50 ml of the medium charged into a 500 ml culture flask), cultured in a shaking incubator at 28-30° C. at a rotational speed of 250-300 rpm, and harvested until the strains grown to OD600=20-30.

(2) It was centrifuged at 5,000 rpm at room temperature for 5 min, removed the supernatant, and collected the cells, which were resuspended with 50 ml BMMY (BMMY: 2% peptone, 1% yeast extract, 1% ammonium sulfate, 0.34% YNB, 100 mmol/L PBS pH 6.0)

And then continued to be cultured in a shaking incubator at 28-30° C. at a rotational speed of 250-300 rpm.

(3) Methanol was added into the shaking flask until a final concentration of 1% every 24 h to achieve induction expression.

(4) 1 ml of culture solution was transferred into a 1.5 ml centrifuge tube at each of the following time points (24 h, 48 h, 72 h, 96 h, 120 h, 144 h, 168 h), and centrifuged at 5,000 rpm at room temperature for 5 min, and collected the supernatant which was stored in a 4° C. refrigerator for use.

(5) After all samples which were cultured for continuous 7 days have been collected, 40 ul of the culture supernatant taken from each sample at every time point was transferred into a new 1.5 ml Eppendorf tube respectively, each added with 10 ul of a treating solution for the protein sample (5×SDS-PAGE Loading buffer 100 ml: 1 mol/L Tris-HCl pH 6.8: 25 ml; glycerol: 50 ml; SDS: 10 g; bromophenol blue: 0.5 g; mercaptoethanol: 5.0 ml; double distilled water: metered to 100 ml), and after mixed uniformly, placed into a boiling water bath for denaturation for 10 min. For each sample, 30 ul was sampled to SDS-PAGE electrophoresis to observe the expression.

(6) Conditions for electrophoresis: spacer gel 4%, separation gel 12%, the electrophoresis buffer being Tris-Glycine Buffer (5×TGB 1 L: Tris base 15.1 g, Glycine 94 g, SDS 5 g, which were dissolved in 800 ml ddH$_2$O, and then re-metered to 1 L), the staining solution being Coomassie Brilliant Blue, and destaining solution being 95% ethanol: glacial acetic acid:water=4.5:0.5:5(V:V:V).

Figure 9:
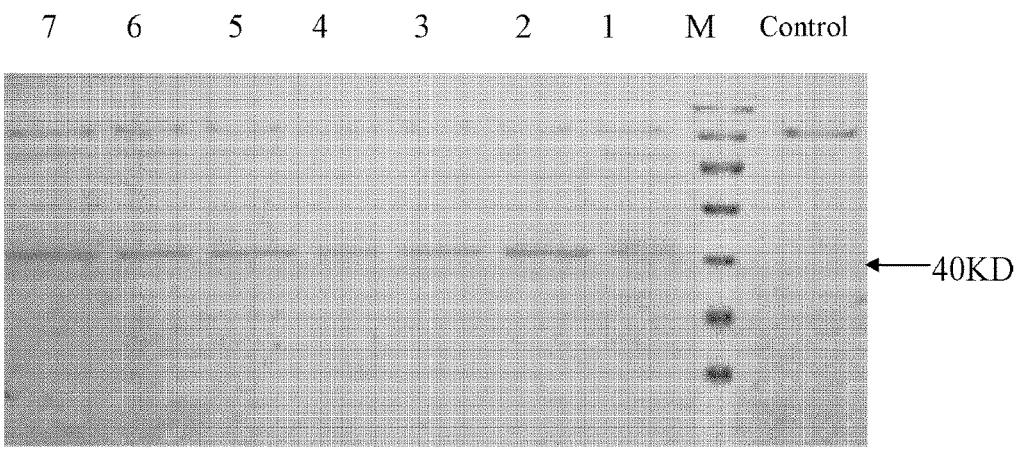
FIG. 9 shows a SDS-PAGE image of the inducted expression of the PprI protein in the pHBM-Pi-pprI *Pichia* transformant, wherein the control lane is the culture supernatant of the pHBM905A *Pichia* transformant as the negative control; lanes 1-7 are culture supernatants of the pHBM-Pi-pprI *Pichia* transformant after induction for 1-7 days, respectively, with a loading amount of 30 µl (which corresponds to 24 µl of the culture supernatant) for each lane; lane M is Marker.

Results showed that, a band of PprI protein secretory expression could be detected with induction for 24 h, and with the prolonging of the induction time, the amount of the PprI protein expression was also gradually increased, which reaches the highest when induction for 120 h, and then tends to be stable (with the electrophoretogram set forth in FIG. 9). In this figure, the PprI protein has a molecular weight of about 43 kD, suggesting that there may be glycosylated modification in this protein.

EXAMPLE 7

Western Blot Detection of the Expression Product from a Recombinant Engineered *Pichia* Strain (pHBM-Pi-pprI *Pichia* Transformant)

Figure 10:
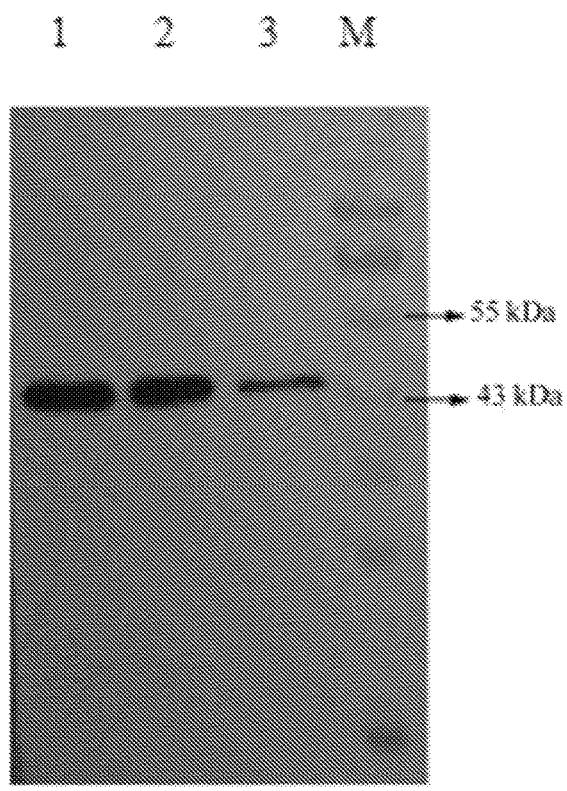
FIG. 10 shows Western Blot detection of the pHBM-Pi-pprI *Pichia* transformant, wherein 1 is the fermented supernatant of the first positive *Pichia* transformant with induction for 2 days; 2 is the fermented supernatant of the second positive *Pichia* transformant with induction for 2 days; 3 is the fermented supernatant of the first positive *Pichia* transformant with induction for 1 day; and lane M is Marker, with a loading amount of 16 µl of the culture supernatant for each lane.

In order to judge whether the specifically expressed protein in the culture supernatant from the recombinant engineered *Pichia* strain (pHBM-Pi-pprI *Pichia* transformant) was indeed a 6× His-PprI fusion protein, in the present invention, 2 positive pHBM-Pi-pprI *Pichia* transformants were randomly selected therefrom and subjected to Western Blot detection with their methanol-induced culture supernatants, set forth in FIG. 10. Results showed that the anti-6× His tag antibody can specifically bind to the protein band adjacent to the position for 43 kDa in the culture supernatants of the 2 positive pHBM-Pi-pprI *Pichia* transformants, and the reaction intensity was correspondingly enhanced with the methanol induction time increasing, suggesting that the specific protein in the culture supernatants of the pHBM-Pi-pprI *Pichia* transformants was a 6× His-PprI fusion protein.

EXAMPLE 8

Mass Spectrum Identification of the Expression Product from a Recombinant Engineered *Pichia* Strain (pHBM-Pi-pprI *Pichia* Transformant)

In order to verify whether the protein in the supernatant from expression of the *Pichia* transformant was PprI protein of *Deinococcus radiodurans*, in the present invention, the protein band of interest which was separated by the gel for SDS-PAGE electrophoresis in Example 6 was cut, and detected for the Peptide Mass Fingerprinting (PMF) with Ultraflex II TOF/TOF mass spectrometer. The detection results were input into OMOSSA database of the National Center for Biotechnology Information (NCBI) for analysis.

The protein of interest was processed as follows:

1) The band of interest was cut with a gel-cutting pen and placed into a centrifuge tube.

2) It was washed with 50 μl of double distilled water twice, each for 10 min.

3) 50 μl of a destaining solution (50 mM $NH_4HCO_3$: $CH_3CN$=1:1) was added for destaining at 37° C. for 20 min.

4) The step 3) was repeated until the blue color was taken off.

5) The gel strip was dehydrated with addition of 50 μl $CH_3CN$ until a white color, and dried under vacuum for 10 min.

6) 50 μl of 10 mM DTT (formulated with 25 mM $NH_4HCO_3$) was added and kept in 56° C. water bath for 1 h.

7) The sample was cooled to room temperature, removed the solution, and rapidly added with 50 μl of 30-40 mM IAA (formulated with 25 mM $NH_4HCO_3$) and placed into a dark room for 45 min.

8) The gel strip was washed successively with 25 mM $NH_4HCO_3$, 25 mM $NH_4HCO_3$+50% $CH_3CN$ twice, each for 10 min, and then dehydrated with $CH_3CN$ again until the gel strip became white, dried under vacuum for 10 min.

9) To each tube was added with 2-3 μl of 0.1 μg/μl Trypsin solution which has been diluted for 10-20 folds with 25 mM $NH_4HCO_3$, and after transient centrifugation, the solution was allowed to come into fully contact with the gel strip, kept at 4° C. for 30 min. After the zymolyte was absorbed completely, 25 mM $NH_4HCO_3$ was added to a total volume of 10-15 μl, and the resultant was kept overnight at 37° C.

10) The reaction was stopped with addition of 2 μl 0.1% TFA, which was mixed uniformly by shaking, centrifuged and collected the zymolyte for point targeting.

Figure 11:
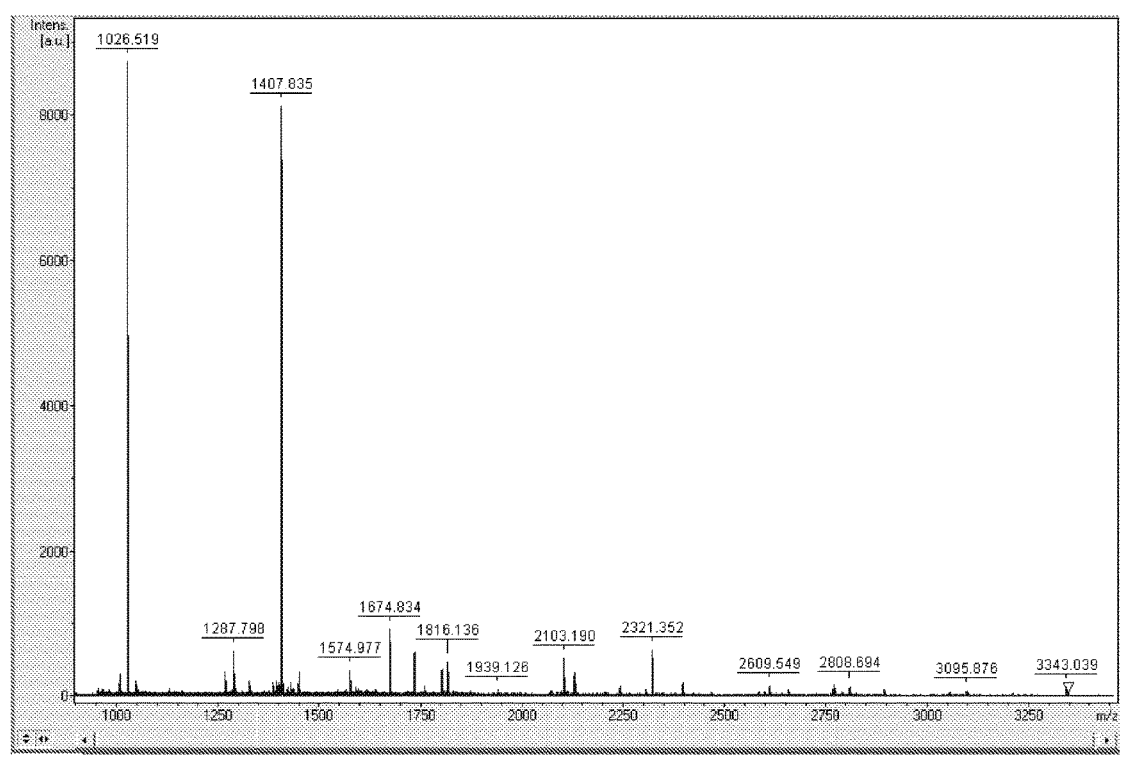
FIG. 11 shows a peptide mass fingerprinting (PMF) of the pHBM-Pi-pprI *Pichia* transformant on Ultraflex II TOF/TOF mass spectrometer.

11) The molecular weight of the peptide fragments were detected by Peptide Mass Fingerprinting (PMF) analysis with Ultraflex II TOF/TOF mass spectrometer from Bruker Daltonics Corp. in USA to be in the range of 900-4000 (m/z, with z being one unit positive charge) (set forth in FIG. 11).

Search analysis on the PMF results resulted from the mass spectrometry was performed by logging in the NCBI nr database from the web of the US National Center for Biotechnology Information (www.ncbi.nlm.nih.gov) and selecting bacteria as the species. Results showed that this protein sequence is indeed a protein derived from *Deinococcus radiodurans* (NP_293891.1). It is suggested that the recombinant engineered *Pichia* strain containing a Pi-pprI gene sequence successfully expressed and secreted the PprI protein of *Deinococcus radiodurans*.

The foregoing description is only the preferred embodiments of the present invention, and it should be indicated that, for those ordinary skilled in the art, several improvements and modifications can also be made without departing from the principle of the present invention, which should be also deemed to be within the protection scope of the present invention.

SEQUENCE LISTING

```
<110> ZHANGJIAGANG INSTITUTE OF INDUSTRIAL TECHNOLOGIES,
SOOCHOW UNIVERSITY
<120> A DNA MOLECULE, RECOMBINANT PICHIA PLASMID AND
RECOMBINANT PICHIA STRAIN EFFICIENTLY EXPRESSING PPRI PROTEIN
OF DEINOCOCCUS RADIODURANS
<130>  10001.0016
<160>     42
<170>  PatentIn version 3.3

<210>      1
<211>    987
<212>  DNA
<213>  Artificial Sequence

<220>
<223>  DNA sequence of Pi-pprI

<400>      1
atgccatctg ctaacgtttc tccaccatgt ccaagtggtg ttagaggcgg tggcatgggt      60
cctaaagcta aggcagaggc ttctaagcca catcctcaga taccagtaaa gttgccattt     120
gttactgcac cagatgcttt ggccgctgct aaagccagaa tgcgtgattt ggctgccgct     180
tatgtagcag cattgccagg tagagatact cattctttga tggctggtgt gccaggagtt     240
gatttgaagt ttatgccatt gggttggagg gatggtgcat ttgatccaga acataacgta     300
attctgatta acagtgcagc tagacctgaa agacaaagat ttacattggc tcatgaaatc     360
ggacatgcta ttttgttggg tgatgatgat ttgttgtccg atattcatga tgcttacgaa     420
ggtgagagat tggaacaagt tattgaaact ttgtgtaatg ttgccgcagc agccatactg     480
atgccagaac cagttatagc cgaaatgttg gaaagattcg gtccaactgg tagagcattg     540
gcagaattgg ctaagagagc agaagttagt gcttcctctg ctttgtacgc tttgactgaa     600
caaacaccag tacctgttat ctacgctgtt tgtgctccag gtaagcctcc aagagaacaa     660
gcagcttccg acgaagatgc cggtccatct actgaaaagg ttttaactgt tagggcctct     720
```

| SEQUENCE LISTING |
| --- |

```
tcttccacta gaggtgttaa gtacactctt gcttctggta ctccagttcc agctgatcat    780
cctgcagcct tggcattagc tacgggtatg gaagtcagag aagagtctta cgttccattt    840
agatctggta ggaaaatgaa ggctgaagtt gatgcatacc catctagagg aattgttgca    900
gtttctitig aatttgaccc agccagatg ggtagaaagg attctgagca ggctgataga    960
gatgaaccac aagatgctgc ccaataa                                        987
```

```
<210>   2
<211>   30
<212>   DNA
<213>   Artificial Sequence

<220>
<223>   DNA sequence of primer

<400>   2
gtcagttcca tctgctaacg tttctccacc                                      30

<210>   3
<211>   46
<212>   DNA
<213>   Artificial Sequence

<220>
<223>   DNA sequence of primer

<400>   3
cctctaacac cacttggaca tggtggagaa acgttagcag atggaa                    46

<210>   4
<211>   46
<212>   DNA
<213>   Artificial Sequence

<220>
<223>   DNA sequence of primer

<400>   4
atgtccaagt ggtgttagag gcggtggcat gggtcctaaa gctaag                    46

<210>   5
<211>   46
<212>   DNA
<213>   Artificial Sequence

<220>
<223>   DNA sequence of primer

<400>   5
tgaggatgtg gcttagaagc ctctgcctta gctttaggac ccatgc                    46

<210>   6
<211>   46
<212>   DNA
<213>   Artificial Sequence

<220>
<223>   DNA sequence of primer

<400>   6
gcttctaagc cacatcctca gataccagta aagttgccat ttgtta                    46

<210>   7
<211>   46
<212>   DNA
<213>   Artificial Sequence

<220>
<223>   DNA sequence of primer

<400>   7
agcggccaaa gcatctggtg cagtaacaaa tggcaacttt actggt                    46

<210>   8
<211>   46
<212>   DNA
<213>   Artificial Sequence
```

-continued

SEQUENCE LISTING

<220>
<223> DNA sequence of primer

<400>    8
cagatgcttt ggccgctgct aaagccagaa tgcgtgattt ggctgc          46

<210>    9
<211>    46
<212>   DNA
<213>   Artificial Sequence

<220>
<223> DNA sequence of primer

<400>    9
tctacctggc aatgctgcta cataagcggc agccaaatca cgcatt          46

<210>    10
<211>    46
<212>   DNA
<213>   Artificial Sequence

<220>
<223> DNA sequence of primer

<400>    10
gcagcattgc caggtagaga tactcattct ttgatggctg gtgtgc          46

<210>    11
<211>    46
<212>   DNA
<213>   Artificial Sequence

<220>
<223> DNA sequence of primer

<400>    11
aatggcataa acttcaaatc aactcctggc acaccagcca tcaaag          46

<210>    12
<211>    46
<212>   DNA
<213>   Artificial Sequence

<220>
<223> DNA sequence of primer

<400>    12
agttgatttg aagtttatgc cattgggttg gagggatggt gcattt          46

<210>    13
<211>    46
<212>   DNA
<213>   Artificial Sequence

<220>
<223> DNA sequence of primer

<400>    13
aatcagaatt acgttatgtt ctggatcaaa tgcaccatcc ctccaa          46

<210>    14
<211>    46
<212>   DNA
<213>   Artificial Sequence

<220>
<223> DNA sequence of primer

<400>    14
tccagaacat aacgtaattc tgattaacag tgcagctaga cctgaa          46

<210>    15
<211>    46
<212>   DNA
<213>   Artificial Sequence

SEQUENCE LISTING

```
<220>
<223> DNA sequence of primer

<400>   15
ttcatgagcc aatgtaaatc tttgtctttc aggtctagct gcactg                46

<210>   16
<211>   46
<212>  DNA
<213>  Artificial Sequence

<220>
<223> DNA sequence of primer

<400>   16
caaagattta cattggctca tgaaatcgga catgctattt tgttgg                46

<210>   17
<211>   46
<212>  DNA
<213>  Artificial Sequence

<220>
<223> DNA sequence of primer

<400>   17
atatcggaca acaaatcatc atcacccaac aaaatagcat gtccga                46

<210>   18
<211>   46
<212>  DNA
<213>  Artificial Sequence

<220>
<223> DNA sequence of primer

<400>   18
gtgatgatga tttgttgtcc gatattcatg atgcttacga aggtga                46

<210>   19
<211>   46
<212>  DNA
<213>  Artificial Sequence

<220>
<223> DNA sequence of primer

<400>   19
agtttcaata acttgttcca atctctcacc ttcgtaagca tcatga                46

<210>   20
<211>   46
<212>  DNA
<213>  Artificial Sequence

<220>
<223> DNA sequence of primer

<400>   20
gagattggaa caagttattg aaactttgtg taatgttgcc gcagca                46

<210>   21
<211>   46
<212>  DNA
<213>  Artificial Sequence

<220>
<223> DNA sequence of primer

<400>   21
ctataactgg ttctggcatc agtatggctg ctgcggcaac attaca                46

<210>   22
<211>   46
<212>  DNA
<213>  Artificial Sequence
```

SEQUENCE LISTING

```
<220>
<223> DNA sequence of primer

<400>    22
ctgatgccag aaccagttat agccgaaatg ttggaaagat tcggtc                    46

<210>    23
<211>    46
<212>  DNA
<213>  Artificial Sequence

<220>
<223> DNA sequence of primer

<400>    23
attctgccaa tgctctacca gttggaccga atctttccaa catttc                    46

<210>    24
<211>    46
<212>  DNA
<213>  Artificial Sequence

<220>
<223> DNA sequence of primer

<400>    24
tggtagagca ttggcagaat tggctaagag agcagaagtt agtgct                    46

<210>    25
<211>    46
<212>  DNA
<213>  Artificial Sequence

<220>
<223> DNA sequence of primer

<400>    25
cagtcaaagc gtacaaagca gaggaagcac taacttctgc tctctt                    46

<210>    26
<211>    46
<212>  DNA
<213>  Artificial Sequence

<220>
<223> DNA sequence of primer

<400>    26
tgcttttgtac gctttgactg aacaaacacc agtacctgtt atctac                   46

<210>    27
<211>    46
<212>  DNA
<213>  Artificial Sequence

<220>
<223> DNA sequence of primer

<400>    27
ggcttacctg gagcacaaac agcgtagata acaggtactg gtgttt                    46

<210>    28
<211>    46
<212>  DNA
<213>  Artificial Sequence

<220>
<223> DNA sequence of primer

<400>    28
ttgtgctcca ggtaagcctc caagagaaca agcagcttcc gacgaa                    46

<210>    29
<211>    46
<212>  DNA
<213>  Artificial Sequence
```

SEQUENCE LISTING

```
<220>
<223> DNA sequence of primer

<400>   29
aaaccttttc agtagatgga ccggcatctt cgtcggaagc tgcttg             46

<210>   30
<211>   46
<212>  DNA
<213>  Artificial Sequence

<220>
<223> DNA sequence of primer

<400>   30
ggtccatcta ctgaaaaggt tttaactgtt agggcctctt cttcca             46

<210>   31
<211>   46
<212>  DNA
<213>  Artificial Sequence

<220>
<223> DNA sequence of primer

<400>   31
aagcaagagt gtacttaaca cctctagtgg aagaagaggc cctaac             46

<210>   32
<211>   46
<212>  DNA
<213>  Artificial Sequence

<220>
<223> DNA sequence of primer

<400>   32
ggtgttaagt acactcttgc ttctggtact ccagttccag ctgatc             46

<210>   33
<211>   46
<212>  DNA
<213>  Artificial Sequence

<220>
<223> DNA sequence of primer

<400>   33
cgtagctaat gccaaggctg caggatgatc agctggaact ggagta             46

<210>   34
<211>   46
<212>  DNA
<213>  Artificial Sequence

<220>
<223> DNA sequence of primer

<400>   34
agccttggca ttagctacgg gtatggaagt cagagaagag tcttac             46

<210>   35
<211>   46
<212>  DNA
<213>  Artificial Sequence

<220>
<223> DNA sequence of primer

<400>   35
ttcctaccag atctaaatgg aacgtaagac tcttctctga cttcca             46

<210>   36
<211>   46
<212>  DNA
<213>  Artificial Sequence
```

SEQUENCE LISTING

```
<220>
<223> DNA sequence of primer

<400>  36
gttccattta gatctggtag gaaaatgaag gctgaagttg atgcat          46

<210>  37
<211>  46
<212> DNA
<213> Artificial Sequence

<220>
<223> DNA sequence of primer

<400>  37
aactgcaaca attcctctag atgggtatgc atcaacttca gccttc          46

<210>  38
<211>  46
<212> DNA
<213> Artificial Sequence

<220>
<223> DNA sequence of primer

<400>  38
catctagagg aattgttgca gtttcttttg aatttgaccc agccag          46

<210>  39
<211>  46
<212> DNA
<213> Artificial Sequence

<220>
<223> DNA sequence of primer

<400>  39
ctgctcagaa tcctttctac ccaatctggc tgggtcaaat tcaaaa          46

<210>  40
<211>  46
<212> DNA
<213> Artificial Sequence

<220>
<223> DNA sequence of primer

<400>  40
ggtagaaagg attctgagca ggctgataga gatgaaccac aagatg          46

<210>  41
<211>  30
<212> DNA
<213> Artificial Sequence

<220>
<223> DNA sequence of primer

<400>  41
ggccattatt gggcagcatc ttgtggttca                            30

<210>  42
<211>  47
<212> DNA
<213> Artificial Sequence

<220>
<223> DNA sequence of primer

<400>  42
gtcacatcat caccaccatc atgttccatc tgctaacgtt tctccac         47
```

SEQUENCE LISTING

<160> NUMBER OF SEQ ID NOS: 42

<210> SEQ ID NO 1
<211> LENGTH: 987
<212> TYPE: DNA
<213> ORGANISM: Artificial Sequence
<220> FEATURE:
<223> OTHER INFORMATION: DNA sequence of Pi-pprI

<400> SEQUENCE: 1

```
atgccatctg ctaacgtttc tccaccatgt ccaagtggtg ttagaggcgg tggcatgggt      60
cctaaagcta aggcagaggc ttctaagcca catcctcaga taccagtaaa gttgccattt     120
gttactgcac cagatgcttt ggccgctgct aaagccagaa tgcgtgattt ggctgccgct     180
tatgtagcag cattgccagg tagagatact cattctttga tggctggtgt gccaggagtt     240
gatttgaagt ttatgccatt gggttggagg gatggtgcat tgatccaga acataacgta      300
attctgatta acagtgcagc tagacctgaa agacaaagat ttacattggc tcatgaaatc     360
ggacatgcta ttttgttggg tgatgatgat tgttgtccg atattcatga tgcttacgaa      420
ggtgagagat tggaacaagt tattgaaact ttgtgtaatg ttgccgcagc agccatactg     480
atgccagaac cagttatagc cgaaatgttg gaaagattcg gtccaactgg tagagcattg     540
gcagaattgg ctaagagagc agaagttagt gcttcctctg ctttgtacgc tttgactgaa     600
caaacaccag tacctgttat ctacgctgtt tgtgctccag gtaagcctcc aagagaacaa     660
gcagcttccg acgaagatgc cggtccatct actgaaaagg ttttaactgt tagggcctct     720
tcttccacta gaggtgttaa gtacactctt gcttctggta ctccagttcc agctgatcat     780
cctgcagcct tggcattagc tacgggtatg gaagtcagag aagagtctta cgttccattt     840
agatctggta ggaaaatgaa ggctgaagtt gatgcatacc catctagagg aattgttgca     900
gtttcttttg aatttgaccc agccagattg ggtagaaagg attctgagca ggctgataga     960
gatgaaccac aagatgctgc ccaataa                                         987
```

<210> SEQ ID NO 2
<211> LENGTH: 30
<212> TYPE: DNA
<213> ORGANISM: Artificial Sequence
<220> FEATURE:
<223> OTHER INFORMATION: DNA sequence of primer

<400> SEQUENCE: 2

```
gtcagttcca tctgctaacg tttctccacc                                       30
```

<210> SEQ ID NO 3
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 3

```
cctctaacac cacttggaca tggtggagaa acgttagcag atggaa                     46
```

<210> SEQ ID NO 4
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 4
atgtccaagt ggtgttagag gcggtggcat gggtcctaaa gctaag    46

<210> SEQ ID NO 5
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 5
tgaggatgtg gcttagaagc ctctgcctta gctttaggac ccatgc    46

<210> SEQ ID NO 6
<211> LENGTH: 46
<212> TYPE: DNA
<213> ORGANISM: Artificial Sequence
<220> FEATURE:
<223> OTHER INFORMATION: DNA sequence of

<400> SEQUENCE: 6
gcttctaagc cacatcctca gataccagta aagttgccat ttgtta    46

<210> SEQ ID NO 7
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 7
agcggccaaa gcatctggtg cagtaacaaa tggcaacttt actggt    46

<210> SEQ ID NO 8
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 8
cagatgcttt ggccgctgct aaagccagaa tgcgtgattt ggctgc    46

<210> SEQ ID NO 9
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 9
tctacctggc aatgctgcta cataagcggc agccaaatca cgcatt    46

<210> SEQ ID NO 10
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 10
gcagcattgc caggtagaga tactcattct ttgatggctg gtgtgc    46

<210> SEQ ID NO 11
<211> LENGTH: 46
<212> TYPE: DNA

<213> ORGANISM: Artificial Sequence
<220> FEATURE:
<223> OTHER INFORMATION: DNA sequence of

<400> SEQUENCE: 11
aatggcataa acttcaaatc aactcctggc acaccagcca tcaaag       46

<210> SEQ ID NO 12
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 12
agttgatttg aagtttatgc cattgggttg gagggatggt gcattt       46

<210> SEQ ID NO 13
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 13
aatcagaatt acgttatgtt ctggatcaaa tgcaccatcc ctccaa       46

<210> SEQ ID NO 14
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 14
tccagaacat aacgtaattc tgattaacag tgcagctaga cctgaa       46

<210> SEQ ID NO 15
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 15
ttcatgagcc aatgtaaatc tttgtctttc aggtctagct gcactg       46

<210> SEQ ID NO 16
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 16
caaagattta cattggctca tgaaatcgga catgctattt tgttgg       46

<210> SEQ ID NO 17
<211> LENGTH: 46
<212> TYPE: DNA
<213> ORGANISM: Artificial Sequence
<220> FEATURE:
<223> OTHER INFORMATION: DNA sequence of

<400> SEQUENCE: 17
atatcggaca caaatcatc atcacccaac aaaatagcat gtccga       46

<210> SEQ ID NO 18
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 18
gtgatgatga tttgttgtcc gatattcatg atgcttacga aggtga         46

<210> SEQ ID NO 19
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 19
agtttcaata acttgttcca atctctcacc ttcgtaagca tcatga         46

<210> SEQ ID NO 20
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 20
gagattggaa caagttattg aaactttgtg taatgttgcc gcagca         46

<210> SEQ ID NO 21
<211> LENGTH: 46
<212> TYPE: DNA
<213> ORGANISM: Artificial Sequence
<220> FEATURE:
<223> OTHER INFORMATION: DNA sequence of

<400> SEQUENCE: 21
ctataactgg ttctggcatc agtatggctg ctgcggcaac attaca         46

<210> SEQ ID NO 22
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 22
ctgatgccag aaccagttat agccgaaatg ttggaaagat tcggtc         46

<210> SEQ ID NO 23
<211> LENGTH: 46
<212> TYPE: DNA
<213> ORGANISM: Artificial Sequence
<220> FEATURE:
<223> OTHER INFORMATION: DNA sequence of

<400> SEQUENCE: 23
attctgccaa tgctctacca gttggaccga atctttccaa catttc         46

<210> SEQ ID NO 24
<211> LENGTH: 46
<212> TYPE: DNA
<213> ORGANISM: Artificial Sequence
<220> FEATURE:

<223> OTHER INFORMATION: DNA sequence of primer

<400> SEQUENCE: 24
tggtagagca ttggcagaat tggctaagag agcagaagtt agtgct                    46

<210> SEQ ID NO 25
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 25
cagtcaaagc gtacaaagca gaggaagcac taacttctgc tctctt                    46

<210> SEQ ID NO 26
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 26
tgctttgtac gctttgactg aacaaacacc agtacctgtt atctac                    46

<210> SEQ ID NO 27
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 27
ggcttacctg gagcacaaac agcgtagata acaggtactg gtgttt                    46

<210> SEQ ID NO 28
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 28
ttgtgctcca ggtaagcctc caagagaaca agcagcttcc gacgaa                    46

<210> SEQ ID NO 29
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 29
aaaccttttc agtagatgga ccggcatctt cgtcggaagc tgcttg                    46

<210> SEQ ID NO 30
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 30
ggtccatcta ctgaaaaggt tttaactgtt agggcctctt cttcca                    46

```
<210> SEQ ID NO 31
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 31
aagcaagagt gtacttaaca cctctagtgg aagaagaggc cctaac            46

<210> SEQ ID NO 32
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 32
ggtgttaagt acactcttgc ttctggtact ccagttccag ctgatc            46

<210> SEQ ID NO 33
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 33
cgtagctaat gccaaggctg caggatgatc agctggaact ggagta            46

<210> SEQ ID NO 34
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 34
agccttggca ttagctacgg gtatggaagt cagagaagag tcttac            46

<210> SEQ ID NO 35
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 35
ttcctaccag atctaaatgg aacgtaagac tcttctctga cttcca            46

<210> SEQ ID NO 36
<211> LENGTH: 46
<212> TYPE: DNA
<213> ORGANISM: Artificially synthesized
<220> FEATURE:
<223> OTHER INFORMATION: DNA sequence of primer

<400> SEQUENCE: 36
gttccattta gatctggtag gaaaatgaag gctgaagttg atgcat            46

<210> SEQ ID NO 37
<211> LENGTH: 46
<212> TYPE: DNA
<213> ORGANISM: Artificial Sequence
<220> FEATURE:
<223> OTHER INFORMATION: DNA sequence of primer
```

```
<400> SEQUENCE: 37
aactgcaaca attcctctag atgggtatgc atcaacttca gccttc          46

<210> SEQ ID NO 38
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 38
catctagagg aattgttgca gtttcttttg aatttgaccc agccag          46

<210> SEQ ID NO 39
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 39
ctgctcagaa tcctttctac ccaatctggc tgggtcaaat tcaaaa          46

<210> SEQ ID NO 40
<211> LENGTH: 46
<212> TYPE: DNA
<213> ORGANISM: Artificial Sequence
<220> FEATURE:
<223> OTHER INFORMATION: DNA sequence of primer

<400> SEQUENCE: 40
ggtagaaagg attctgagca ggctgataga gatgaaccac aagatg          46

<210> SEQ ID NO 41
<211> LENGTH: 30
<212> TYPE: DNA
<213> ORGANISM: Artificial Sequence
<220> FEATURE:
<223> OTHER INFORMATION: DNA sequence of primer

<400> SEQUENCE: 41
ggccattatt gggcagcatc ttgtggttca                            30

<210> SEQ ID NO 42
<211> LENGTH: 47
<212> TYPE: DNA
<213> ORGANISM: Artificial Sequence
<220> FEATURE:
<223> OTHER INFORMATION: DNA sequence of primer

<400> SEQUENCE: 42
gtcacatcat caccaccatc atgttccatc tgctaacgtt tctccac         47
```

What is claimed is:

1. A DNA molecule comprising the nucleotide sequence set forth in SEQ ID NO: 1.

2. The DNA molecule according to claim 1, wherein the nucleotide sequence set forth in SEQ ID NO: 1 is obtained by overlapping PCR amplification from the primers of the nucleotide sequences set forth in SEQ ID NOs: 2-41.

3. The DNA molecule according to claim 1, wherein it comprises the nucleotide sequence set forth in SEQ ID NO: 1 and a 6× His tag sequence, with the 6× His tag sequence being located at the 5'-end of the nucleotide sequence set forth in SEQ ID NO: 1.

4. A recombinant *Pichia* plasmid, wherein it is obtained by insertion of a DNA molecule comprising the nucleotide sequence set forth in SEQ ID NO: 1 into a *Pichia* expression plasmid.

5. The recombinant *Pichia* plasmid according to claim 4, wherein it is obtained by insertion of a DNA molecule comprising the nucleotide sequence set forth in SEQ ID NO: 1 and a 6× His tag sequence between the CpoI and the NotI cleavage sites in pHBM-905A plasmid, wherein the 6 × His tag sequence is located at the 5'-end of the nucleotide sequence set forth in SEQ ID NO: 1.

6. A recombinant engineered *Pichia* strain, characterized in that it is obtained by transformation of the recombinant *Pichia* plasmid according to claim 4 into a competent *Pichia* cell.

7. The recombinant engineered *Pichia* strain according to claim 6, characterized in that it is obtained by linearization of the recombinant *Pichia* plasmid by Sal I cleavage, and then electrotransformation of the linearized plasmid into a competent *Pichia* GS115 cell.

8. A method for preparing PprI protein, comprising culturing the recombinant engineered *Pichia* strain according to claim 6, and collecting the culture supernatant containing the Pprl protein.

9. The method according to claim 8, further comprising induction expression of the PprI protein from the recombinant engineered *Pichia* strain, and purification of the PprI protein.

\* \* \* \* \*